United States Patent [19]
Clarke et al.

[11] 3,945,835
[45] Mar. 23, 1976

[54] HEAVY DUTY AQUEOUS WOOD PRESERVATIVE

[75] Inventors: Michael R. Clarke; Jaromir R. Rak, both of Ottawa, Canada

[73] Assignee: Canadian Patents and Development Limited, Ottawa, Canada

[22] Filed: May 21, 1973

[21] Appl. No.: 362,104

[30] Foreign Application Priority Data
Dec. 12, 1972    Canada................................ 158685

[52] U.S. Cl................ 106/15 R; 106/243; 424/134; 424/141; 427/440
[51] Int. Cl.²............................................ C09D 5/14
[58] Field of Search ........ 106/15 AF, 243; 424/134, 424/141; 427/440

[56] References Cited
UNITED STATES PATENTS

| | | | |
|---|---|---|---|
| 2,310,257 | 2/1943 | Ritter........................... | 106/15 AF X |
| 2,414,661 | 1/1947 | Nikitin......................... | 106/15 AF X |
| 2,423,619 | 7/1947 | Roon ........................... | 106/15 AF X |
| 2,573,252 | 10/1951 | Farber......................... | 106/15 AF X |

FOREIGN PATENTS OR APPLICATIONS
568,393    1/1959    Canada

OTHER PUBLICATIONS
Rose, *The Condensed Chemical Dictionary*, 7th Ed., N.Y. Van Nostrand Reinhold Company, 1966. (pp. 247 and 1031 relied on).

*Primary Examiner*—Lorenzo B. Hayes
*Attorney, Agent, or Firm*—Flynn & Frishauf

[57] ABSTRACT

An aqueous wood treating and/or preservative composition is provided. The composition has a pH of 9 or more. Of the ions present in the composition, the cations are copper ammonium and/or zinc ammonium ions, while the anions include arsenic or arsenious ions, as well as further anions of an acid ester of phosphoric acid or carbonate or bicarbonate or both such acid ester of phosphoric acid and a, which anions have a solubility of $\geq 0.2\%$ in concentrated (28%) aqueous ammonia. The further anions are derived from components which are insoluble in water. Wood treating procedures and treated wood products so-provided are also provided.

10 Claims, 4 Drawing Figures

FIG. 1.

HEAVY DUTY AQUEOUS WOOD PRESERVATIVE

BACKGROUND OF THE INVENTION

1. Field of the Invention

This invention relates to compositions and procedures for the treatment of wood and wood products. The wood products may be used either as materials which are to have high aesthetic considerations, (e.g. structural lumber for housing, wall planks, siding, window sashes, roof decks, shingles and shakes, stadium seats, picnic tables, farm silos and poles in special areas and hereinafter referred to as "Group I materials") or as materials which are to have low aesthetic considerations, (e.g. foundation piles, poles, posts and fences, ties, marine structures, highway and bridge construction, laminated systems for exterior use, and cooling towers, and hereinafter referred to as "Group II materials"). Such compositions and treatment procedures are designed to provide protection not only during the storage and the handling of the lumber, or as use as a primer of sheathing, but also to provide protection during the final use of the wood and wood products. It also relates to the treated wood products so formed.

2. Description of the Prior Art

A piece of timber, due to the manner of its formation, possesses anisotropic structure which influences its properties and behaviour. Compared to competitive cladding materials, for example metals and plastics materials, it has a number of major disadvantages which tend to counteract the advantages of strength, lightness, low thermal expansion and desirable aesthetic features (for Group I materials). To overcome and minimize these disadvantages a number of specific problems exist: the wood must be protected against degrading environmental factors (namely, moisture cycling, photodegradation and biological attack); the dimensional stability with respect to moisture cycling must be improved; photodegradation due to sunlight must be minimized; the resistance to biological attack (fungus) must be improved; the adhesion of protective and decorative coatings must be improved; and extractives which adversely affect protective and decorative properties of coatings must be sealed within the wood. In the case of Group I materials, moreover, such aims should be achieved with a treatment that does not alter the natural beauty of wood.

Protective systems for both groups should impart not only protection against biological degradation, but also considerable weather resistance. The special needs of Group I materials are high protection against weather, and against biodegradation and, additionally, providing protection against fire and maintaining the natural appearance of wood without discoloration after treatment. The system should provide weather resistance with enhanced fire resistancy and no discoloration after treatment. The treated material should also be clean and paintable.

The desirability of properties for materials with high aesthetic consideration (Group I) and for materials of low aesthetic consideration (Group II) are shown in the following two tables:

Desirability of Properties for Material with High Aesthetic Consideration

| Material | Toxic to Fungi & Insects | Water Repellent | Resistant to Flame Spread | Resistant to Glow Combustion | Clean or Paintable | Not Discolored |
|---|---|---|---|---|---|---|
| Structural lumber for housing | + | + | + | + | + | + |
| Wall planks | +(−) | + | + | + | + | + |
| Siding | + | + | + | + | + | + |
| Window sashes | + | + | + | + | + | + |
| Roof decks | + | + | + | + | + | + |
| Shingles & shakes | + | + | + | + | + | + |
| Stadium seats | − | + | + | − | + | + |
| Picnic tables | + | + | − | − | + | + |
| Farm silos | + | + | − | − | + | +(−) |
| Poles in special areas | + | + | − | + | + | + |

Desirability of Properties for Material with Low Aesthetic Consideration

| Material | Toxic to Fungi & Insects | Water Repellent | Resistant to Flame Spread | Resistant to Glow Combustion | Clean or Paintable | Not Discolored |
|---|---|---|---|---|---|---|
| Foundation piles | + | + | − | − | − | − |
| Poles | + | + | − | + | − | −(+) |
| Posts & fences | + | + | + | + | − | − |
| Ties | + | + | − | −(+) | − | − |
| Marine structures | + | + | −(+) | − | − | − |
| Highway & bridge construction | + | + | − | −(+) | − | − |
| Laminated systems (exterior use) | + | + | − | − | + | − |
| Cooling towers | + | + | − | − | − | − |

Four classes of treatments are currently used in an attempt to meet these requirements, for both Group I materials and Group II materials.

The first class is that of clear or pigmented penetrating systems which contain fungicides and water-repellant additives, such as, for example, polyethylene waxes and metal stearates in a non-aqueous solvent media. These treatments are deficient in that they must be repeated at regular intervals of 1 to 2 years to provide a desired level of protection.

The second class is that of stains and sealers. These are normally synthetic resin solutions, usually pigmented and designed to penetrate the surface of the wood. These treatments as well are deficient, and should be repeated every one or two years in order to provide the required degree of protection.

The third class is that of paint systems. Such paint systems would normally consist of a primer and top coats. When well applied, these will provide the exterior cladding protection from 2 to 5 years.

The fourth class is that of salt treatments. A number of salt treatments have been suggested for Group I materials generally, and as clean systems for Group II materials, the most common of which are known as copper-chrome arsenate (CCA), acid-copper-chromate (ACC) and ammonia-cal copper salts. Presently systems of this type are effective to provide relatively long term durability when applied by pressure impregnation techniques. While such systems are effective in preventing biological deterioration of wood and provide clean and paintable surfaces, they, however, suffer from several disadvantages. CCA preservatives have low stability under storage and processing conditions and penetration into wood is limited. ACC preservatives cannot penetrate refractory species but water repellency of wood treated by ACC is good. Ammoniacal copper salts provide extremely stable treating solutions and produce a treated wood product which is clean, in which the preservative penetrates deeply into the wood substance (particularly in the case of refractory species), but which provides negligible protection to the products against weathering. All systems provide products which are more or less colored; thus the natural appearance of wood is changed or covered by the colored preservative and so is unsuitable for Group I materials. Furthermore, none of these systems provides protection against glowing combustion. The CCA systems are believed to become fixed in the wood by oxidation-reduction reaction associated with the chromic acid in the compositions and it is these same reactions which are believed adversely to affect stability and processing characteristics. Moreover, while providing a high level of protection against fungal attack, they provide only limited protection against weathering.

In the case of Group II materials, two main preserving systems are used, namely, (1) creosote, and (2) pentachlorophenol in pole oil. These preserving systems are effective in (1) preventing fungal and insect attack on the wood substance; and (2) in preventing weathering of the timber. Both of these requirements are important where long life is required in wood exposed to the weather. However, these treatments suffer from several disadvantages. The most important of these is low cleanliness and lack of paintability. Oil in these systems exudes to the surface making the wood unpleasant (dangerous) to handle, impossible to paint, and provides a surface which readily accumulates dirt.

Preservative systems which provide colorless material preserving more or less the natural appearance of the wood and which are suitable for Group I materials, and as clean systems for Group II materials which are available at the present time are the oil-free pentachlorophenol systems using liquified gas or highly chlorinated aliphatic hydrocarbons as a solvent end vehicle for pentachlorophenol. Data indicates that products produced by these processes are inferior in weather resistance to wood products impregnated by oil-borne preservatives. However, the cleanliness and paintability of such products is good. However, treatments with oil-borne preservatives cover up the natural appearance of wood and leave wood generally unsuitable for the application of finishes. Moreover, neither of the above-mentioned systems protects the wood against glowing combustion.

Thus, each of the preserving systems mentioned above has disadvantages and these can be summarized as follows:

The major disadvantage of the use of creosote and pentachlorophenol oil treatment is their low cleanliness and their lack of paintability.

The major disadvantage of the use of copper-chrome-arsenate systems is limited stability of the treating solution under processing conditions.

The major disadvantage of the use of ammoniacal copper compounds is the lack of weathering resistance of the treated wood product.

The major disadvantage of the use of oil-free pentachlorophenol treatments is the lack of weathering properties relative to the creosote and pentachlorophenol-oil systems.

Copper and zinc-containing fungicides which have been proposed, (see U.S. Pat. No. 2,414,661 issued Jan. 21, 1947 to A. A. Nikitin), were prepared by precipitation of a zinc salt and a copper salt from an aqueous solution with an alkali solution containing soya bean protein, or soaps of fatty acids.

Fungicides, which have been proposed for cellulosic materials, (see U.S. Pat. No. 2,423,619 issued July 8, 1947 to L. Roon) comprise copper soaps formed in situ from an aqueous solution of copper salts and aqueous ammonia by reaction with fatty acids.

It has also been proposed to provide water and fire-resistant coatings on wood, (see U.S. Pat. No. 2,530,458 issued Nov. 21, 1950 to H. R. Frisch) by the use of zinc orthophosphate or zinc orthoarsenate compositions applied as a concentrated solution in aqueous ammonia.

It has been proposed, (see U.S. Pat. No. 2,768,910 issued Oct. 30, 1956 to H. Krzikalla and O. Lissner) to improve the hardness, compressive strength, hygroscopicity and liability to swell of wood by impregnating the wood with an aqueous ammoniacal solution of polycarboxylic acid containing at least six carbon atoms.

It has been proposed, (see U.S. Pat No. 2,772,263 issued Nov. 27, 1956 to C. C. Yeager) to use a compound having a high fungicidal activity in wood, which compound is a metal rosin ammonium phenoxide-complex metal carboxylic acid soap compound, prepared by reacting a rosin ammonium phenoxide with a water-soluble salt of a metal capable of forming a complex with ammonia.

It has also been proposed, (see U.S. Pat. No. 3,007,844 issued Nov. 7, 1961 to W. O. Schuly) to use a composition comprsing a heavy metal ion, borate ions and chromate ions as an impregnating agent for the preservation of wood.

It has further been proposed, (see U.S. Pat. No. 3,105,773 issued Oct. 1, 1963 to S. Frank and D. C. Wehner) to preserve wood by imparting pesticidal and anti-thallophytic properties thereto by first impregnating the wood with a water-soluble heavy metal salt, and then with an acrylic polymer solution.

It has still further been propsed (see U.S. Pat. No. 1,942,977 issued Jan. 9, 1934 to E. E. M. Payne) to treat wood products with a solution of one or more ammonium phosphates and then with a solution containing acid phosphates of magnesium and zinc, in order to precipitate an insoluble phosphate within the cell structure of the material, thereby to improve the color of the materials and to render the treated material resistant to fire.

It has also been proposed, [see British Pat. No. 1,220,281 published Jan. 27, 1971 in the name of Hickson's Timber Impregnation Co. (G.B.) Ltd.] to treat wood with an aqueous emulsion containing an aqueous solution of a wood preservative composition based on hexavalent chromium, a water-insoluble insecticide in a liquid hydrocarbon solvent, and a non-ionic surface active agent. The emulsion is used by impregnation of the wood by means of a pressure process, to provide protection against fungal attack and against a variety of insects.

A paper in the Forest Products Journal, Vol. 20, No. 11, Nov. 1970 by M. P. Levi et al entitled "Distribution and Effectiveness in Pinus Sp. of a Water Repellant additive for Water-Borne Wood Preservatives" discusses the development of a water repellent additive for use with water-borne CCA preservatives to overcome the deficiency of prevention of weathering degradation.

Ammoniacal copper arsenite compositions are presently being used as preservatives. Zinc arsenate, zinc arsenite, and zinc phosphate can all be applied from an acetic acid solution and, on drying, the salt is insoluble and fixed in the wood. However, in all of these cases, the weather resistance of the treated wood is not significantly improved.

While the use of the compositions outlined above has tended to provide a considerable level of protection against specific degrading agencies, none of them provides a suitable balance of properties such as, for example, excellent stability, high weather resistance, paintability, good wood penetration and good water repellency. Additionally some of the compositions outlined provide in the one system not only the protective properties mentioned avove, but also a measure of protection against fire and do not adversely affect the natural appearance of the treated wood.

SUMMARY OF THE INVENTION

1. Main Aims of the Invention

Therefore, prime objectives of this invention are to provide such compositions in which a suitable balanced improvement is provided in the following properties, namely: a good level of weather resistance; low mammalian toxicity; resistance to biological and fungal attack; resistance to water penetration; resistance to extractive staining; substantially no adverse effect on protection against glowing combustion; good adhesion properties between the wood and a coating, e.g. paint or glue, etc. later to be applied thereto; and no substantial adverse effect on lumber seasoning.

2. Broad Statement of the Invention

According to a broad concept of this invention, a wood treating composition is provided which is based on copper and/or zinc ammonium complexes containing arsenic anions ($As^{III}$ or $As^{V}$) and other additives, all components being soluble in one common aqueous ammoniacal solution. In the above-noted composition, the preservative compounds in the form of water-insoluble salts of zinc or copper or a mixture of these are solubilized in admixture with certain specified water repellent compounds in the ammoniacal solution.

3. Variants of the Invention

In other words, in a broad aspect of this invention, a wood treating composition is provided, comprising an aqueous solution containing (a) a normally water-insoluble compound of zinc and/or copper with arsenic acid or arsenious acid in an amount of about 0.1 to about 4% by weight (as Zn or Cu metal) of the total aqueous solution; (b) about 0.15 to about 10% by weight of the total aqueous solution of a water repellent component, such component comprising either (i) a water-insoluble organic acidic compound having a solubility $\geq$ about 0.2% in concentrated aqueous ammonia, in an amount of about 0 to about 200% of the zinc or copper, (ii) carbonate or bicarbonate ions in an amount of about 0 to about 150% of zinc or copper, or (iii) a combination of carbonate ions or bicarbonate ions and the aforesaid water-insoluble organic compound in an amount of about 0 to about 150% of the zinc or copper; and (c) ammonia, in an amount of about 1 to 28% by weight of the total aqueous solution; the ammonia being sufficient to solubilize the normally water-insoluble salt of zinc or copper, and the normally water-insoluble water repellant compound.

The constituents of the preservative composition may range in concentration (expressed as percentage by weight of the total) as follows:

| | | |
|---|---|---|
| 1. | Zinc and/or copper arsenic compound, present as the arsenate or the arsenite | about 0 to about 4 (as Zn or Cu metal) |
| 2. | Water repellent, the water repellent being an organic acidic compound present in proportions ranging between about 0% and about 200% of the zinc or copper; or carbonate or bicarbonate ions present in proportions ranging between about 0% and about 150% of the zinc or copper; or the mixtures thereof | about 0.15 to about 10 |
| | and | |
| 3. | Ammonia | about 1 to about 28 |

By another aspect of this invention, a procedure is provided for protecting cellulosic products which comprises impregnating such cellulosic products by applying an aqueous solution (as described above) to the surfaces of such cellulosic products and then drying the surfaces with the resulting loss of ammonia. Preferably, the impregnation is conducted in such a way as to provide a penetration of at least about ¼ inch (if the cellulosic product is thicker than about ½ inch).

By yet another aspect of this invention, a concentrated preservative composition is provided which includes a zinc or copper arsenic compound or mixtures of zinc and copper arsenic compounds in which the arsenic compound is present as the arsenate or the arsenite, a water-repellent which is an organic acidic compound, and concentrated aqueous ammonia, in which the amounts of the zinc and/or copper are directly proportional to the amount of the arsenic compound, but which generally vary in a soluble amount, up to about 80%, the zinc being present in an amount of about 25% to about 80%; the copper being present in an amount of about 15% to about 25%; and the amount of zinc and copper being present in an amount of about 25% to about 50%; the concentrate being dilutable to give a composition as described above.

4. Further characteristics of the Invention

Whether copper and/or zinc is used, the organic acidic component may generally be defined as an acidic compound which is insoluble in water but which is capable of forming compounds with the metal ammonia complex which are soluble in aqueous ammoniacal solution. The organic acidic component has a solubility of about 0.5%, preferably > about 3% in concentrated aqueous ammonia (about 28%). Such component may be a substantially water-insoluble monocarboxylic acid having between about 8 and about 15 carbon atoms in the carboxylic acid and being either unsubstituted or substituted with hydrocarbon radicals, hydroxyl radicals or halogens. Examples include saturated fatty acids, for example, octanoic, nonanoic (pelargonic), capric (decanoic), lauric (dodecanoic), myristic (tetradecanoic); unsaturated fatty acids, for example, $\Delta^{9,10}$-decylenic, $\Delta^{9,10}$-dodecylenic. The preferred materials are those saturated and unsaturated higher aliphatic acids containing from nine to fifteen carbon atoms. Other organic acidic compounds which may be used are maleinized unsaturated fatty acids or esters from animal or vegetable sources, such as, for example, sardine and other fish oils, lard, coconut oil, sesame oil, soybean oil, tung oil, corn oil, and having an acid value of about 200 to about 500; maleinized unsaturated fatty acids, oils and resins formed by the reaction of maleic acid or maleic alkyds with the fatty polycarboxylic acids having an acid value between about 200 and about 500; aromatic carboxylic acids and derivatives thereof having an acid value between about 200 and about 500; the acid esters of phosphoric acid with monohydric alcohols or fatty alcohols having an acid value between about 200 and about 500; condensation polymers in which the acid value is between about 200 and about 500; and any mixtures of the above.

In the present specification, the term acid value is that given in Sec. 3.1 on page 57 of the text "Modern Surface Coatings" Nylen and Sunderland, Interscience Publishers (1965). The test method to determine "acid value" is given in American Standard Test Method D556-61.

In addition, the term "maleinized" is that given in the descriptions of maleinized oils and maleinized resins given in Sec. 3.6 on Page 113 and in Sec. 5.1 on page 171 respectively of the above-identified text "Modern Surface Coatings".

Other acids which may be used include synthetic polycarboxylic acids such as, for example, polyesters and alkyds having an acid value between about 200 to about 500.

The above-identified organic acidic compounds may be used as the sole water-repellent agent, or may be used in admixture with a carbonate ion, or a bicarbonate ion. The carbonate ion or bicarbonate ion can be provided either by selection of the zinc carbonate, zinc bicarbonate, copper carbonate or copper bicarbonate, or it can be formed by reaction of a suitable zinc or copper salt, e.g., the oxide with ammonium carbonate or ammonium bicarbonate in the ammonia solution. In addition, the carbonate or the bicarbonate may be used as the sole water-repellent agent or may be used in admixture with the above-identified organic acidic compounds.

One way of selecting the organic acidic component is by determining its solubility in a solution of ammonia in water of about 28%. The organic acidic components are characterized in that they form compounds with copper and/or with zinc which are water insoluble, but which are soluble to greater than about 0.2%, preferably greater than about 3%, in an aqueous ammonia solution of about 28%.

If the composition within the ambit of this invention is one containing zinc ions, the wood material provided, according to another aspect of this invention, is one having high aesthetic considerations. The essential presence of arsenic acids or arsenious acids or mixtures thereof in such composition results in a composition which protects the wood against biological degradation. When carboxylic acids and/or carbonic or bicarbonic acid ions are present in the composition, the composition imparts high water repellency and weather resistance to the wood. When carbonic or bicarbonic acid ions or mixtures thereof are present in the composition, the composition imparts protection to the wood against glowing combustion.

If the solution is one containing copper ions, the wood material provided, according to yet another aspect of this invention, is one having low aesthetic considerations. The essential presence of arsenic acids or arsenious acids or mixtures thereof in such composition results in a composition which protects the wood against biological degradation. When carboxylic acids and/or carbonic or bicarbonic acid ions are present in the composition, the composition imparts high water repellency and weather resistance to the wood.

The level of ammonia used in the compositions described above is generally in excess of that required to form the copper or zinc salts or coordinating complexes; the aqueous compositions will generally have a pH of about 9 or higher. The non-volatile solids of the compositions may vary between about 1% and about 25% (in the case of zinc), or between about 1% and about 15% (in the case of copper, or mixtures of copper and zinc).

In one embodiment, compositions for Group I materials are provided. These compositions comprise an aqueous solution of a zinc ammonium arsenate or arsenious complex with the water-repellant additive in the form of carbonate or carboxylic acids, as defined above, which is characterized by its ability to give rapid penetration into wood substance and which on drying leaves wood with its natural appearance and color, resistant to biological deterioration, resistant to weathering and resistant to glowing combustion. The treating solution has excellent stability under processing conditions.

One example of a treating composition according to the specific needs for a material in Group I is:

| | |
|---|---|
| zinc meta arsenite | about 1.5 parts by weight |
| zinc carbonate | about 4.5 parts by weight |
| decanoic acid | about 3 parts by weight |
| aqueous ammonia (about 5% ammonia in water) | about 91 parts by weight |

In another embodiment of the invention, for Group II material use, the composition comprises an aqueous solution of a copper ammonium arsenic or arsenious complex with the water-repellent additive in the form of carbonate or carboxylic acids, as defined above, which is characterized in that it gives rapid penetration into the wood substance and which, on drying, renders the wood resistant to weathering and resistant to biological deterioration. The treating solution has excellent stability under processing conditions.

One example of a composition according to specific needs for a material in Group II is:

| | |
|---|---|
| copper arsenate | about 3 parts by weight |
| copper carbonate | about 3 parts by weight |
| organic additive as e.g. decanoic acid | about 2 parts by weight |
| aqueous ammonia (about 5% ammonia in water) | about 92 parts by weight |

The compositions described for both Group I material and Group II material application may be applied to the wood by known application methods, for example, by brush, spray or dip treatments or by impregnation techniques.

In use, the preservative composition impregnates the wood, and after being dried with the resulting loss of ammonia, the preservative compounds become fixed in the wood substance. The treated wood is resistant against decay and insect attack, has high water repellency, and increased protection against glowing combustion. The composition penetrates efficiently into even refractory species and on drying renders wood highly resistant to weather and to biological attack.

While it is not desired to be limited to any particular theory, it is believed that the high moisture pick-up of wood is due to physical absorption of moisture onto cellulose chains in the microfibrils, resulting in a decrease in the association between neighbouring cellulose chains. It is believed further that the composition changes the hydrophylic nature of the wood surface (both external and internal) to a hydrophobic nature and thereby increases the weather resistance of the treated wood substance.

It is felt that the reduction in moisture pick-up of the treated wood is due to a cross-linking action by the zinc or copper ions between neighbouring cellulose chains. This cross-linking action may well occur due to the high strength of coordination linkages. It is further believed that resistance to photodegradation is associated with the formation of pigment crystals formed within the wood substance which effectively screens the natural polymers from the damaging radiation.

BRIEF DESCRIPTION OF THE DRAWINGS

The present invention may be better understood and its numerous objects and advantages will become apparent to those skilled in the art by reference to the accompanying drawings, in which.

DESCRIPTION OF PREFERRED EMBODIMENTS

The invention in certain of its embodiments is illustrated in the following examples in which all proportions are by weight.

The invention, with respect to compositions for use with Group I materials, is illustrated as follows in Examples I–IV, where all proportions are by weight.

EXAMPLE I

Treating solution preparation

Solutions of the zinc salts and of the organic acidic component, namely nonanoic acid, were prepared in concentrated aqueous ammonia solution (about 28% $NH_3$) at room temperature, and were then diluted with distilled water to give the following formulation:

| | |
|---|---|
| zinc arsenate | 4 parts by weight |
| nonanoic acid | 2 parts by weight |
| zinc carbonate | 1 part by weight |
| aqueous ammonia solution (7%) | 93 parts by weight |

Preservative treatment of wood product

The above-described solution has been used for pressure treating of pole sections of white spruce, 7 in. diameter, 48 in. long. Specimens were loaded in a pressure vessel, which was evacuated to 26 in. Hg vacuum and maintained under vacuum for one hour. Then, the preservative solution was introduced into the pressure vessel and the pressure was increased up to 120 psi with compressed air and was maintained at that pressure for 5 hours. The temperature was increased up to 150°F. during treatment. After the pressure was released, the samples were kept for the next 12 hours immersed in the solution. The retention of the preservative solution in treated specimens was found to be 19 lb/cu.ft. The depth of penetration in the middle of the samples, measured on center cross-sections, was from ½in. to ¾in.

EXAMPLE II

A treating solution was prepared the same way as in Example I, but the concentration and components of solutions were different as follows:

| | |
|---|---|
| zinc arsenate | 4.5 parts by weight |
| zinc carbonate | 2.0 parts by weight |
| monododecyl phosphate | 0.2 parts by weight |

-continued

| | |
|---|---|
| aqueous ammonia solution (7%) | 93.3 parts by weight |

Preservative treatment

The treatment was carried out on red pine pole sections 8 in. diameter and 48 in. long. The treating procedure was the same as in Example I but the initial vacuum was held for 30 minutes only and for 5 hours at 115 psi presure, during which time the specimens were immersed in the preservative solution. An additional period of 5 hours was used to keep the pole sections in the preservative solution without any pressure. The temperature during the pressure treatment was 155°F. The gross retention of the treating solution reached 29.6 lb/cu.ft. and the depth of penetration, measured on center cross-sections, achieved 1¼ to 1½ in.

EXAMPLE III

The following composition was used for non-pressure treatment of white spruce lumber 2 × 4 × 48 inches:

| | |
|---|---|
| zinc arsenate | 1 part by weight |
| decanoic acid | 3 parts by weight |
| zinc carbonate | 3 parts by weight |
| aqueous ammonia solution (10%) | 93 parts by weight |

The treatment was carried out in the same manner as described in Example I starting with an initial 1 hour vacuum, but in which no pressure was applied during 5 hours treatment when the lumber was immersed in the treating solution. The temperature was increased up to 175 °F. in the treating cylinder and was held there for 5 hours. Cooling of the specimens in the preservative solution followed for the next 16 hours. The depth of penetration, on center cross-sections, was observed to be ⅜–½ inch.

EXAMPLE IV

The non-pressure preservative treatment of red pine lumber 2 × 6 × 48 in. was carried out the same way as in Example III. The preservative solution used had the following composition:

| | |
|---|---|
| zinc arsenate | 1 part by weight |
| zinc oxide | 5 parts by weight |
| ammonium carbonate | 2 parts by weight |
| dibutyl phosphate | 0.2 parts by weight |
| aqueous ammonia solution (10%) | 91.8 parts by weight |

After treatment, the depth of preservative penetration was measured on center cross-sections and was found to be from ½ to 1 inch.

The invention, with respect to compositions for use with Group II materials, is illustrated as follows in Examples V–VIII in which all proportions are by weight.

EXAMPLE V

Preparation of preservative treated wood products.

Treating Solution Preparation

Saturated solutions of the copper salts and the organic acidic components, e.g. lauric acid, were prepared in concentrated aqueous ammonia solution (28%) at room temperature. The required amount of these solutions was mixed with water and concentrated ammonia solution (28%) to give the following formulation:

| | |
|---|---|
| copper carbonate | 1 part by weight |
| copper arsenate | 1 part by weight |
| lauric acid | 0.5 parts by weight |
| aqueous ammonia solution (5%) | 98.5 parts by weight |

Preservative Treatment of Wood Products

The treating solution described above was used to treat white spruce lumber and round wood specimens.

| Lumber | |
|---|---|
| Dimensions | 1.8 × 1.8 × 48 inches |
| Moisture content | 8 – 10% |
| Round Wood (logs) | |
| Dimensions | 7 inches diameter × 48 inches long |
| Moisture content | 30% |

The specimens were loaded into a pressure vessel and evacuated to 26 ½ in. Hg and maintained under vacuum for one hour. The pressure was increased in the vessel to 10 in. Hg with ammonia gas before introducing sufficient treating solution completely to cover the specimens. The pressure in the treating vessel was raised to 100 p.s.i. with compressed air. The temperature of the treating solution was raised from 75°F. to 150°F. over the first three-hour period and was reduced to 100°F. over the next three hours while maintaining an overpressure of 100 p.s.i. The pressure was then reduced to 10 p.s.i. before pumping the treating solution back into a hold tank.

The retention of the treating solution in the wood specimens was determined 24 inches from the ends of the specimens and average values were as follows:

| | |
|---|---|
| Lumber | 18 lb/cu.ft. |
| Logs | 23.3 lb/cu.ft. |

EXAMPLE VI

Preparation of preservative treated wood products.

Treating Solution Preparation

A saturated solution of the copper salts along with the organic acidic component, e.g. decanoic acid, was prepared in concentrated aqueous ammonia solution (28%) at room temperature. The required amount of these solutions was mixed with additional decanoic acid, water and concentrated ammonia solution (28%) to give the following formulation:

| | |
|---|---|
| copper arsenate | 3 parts by weight |
| decanoic acid | 3 parts by weight |
| aqueous ammonia solution (7%) | 94 parts by weight |

Preservative Treatment of Wood Products

The treating solution described above was used to treat lumber and log specimens by a pressure impregnation process. The specimens used and the treating schedule were similar to those described in Example V. The results of these tests were equal to those shown in Example V with respect to degree of impregnation.

EXAMPLE VII

Preparation of preservative treated wood products.

Treating Solution Preparation

The copper salts and dihexyl phosphate were mixed for thirty minutes and then taken into solution with concentrated aqueous ammonia solution (28%) at 120°F. The resulting solution was diluted with water and concentrated aqueous ammonia solution (28%) to give the following formulation:

| | |
|---|---|
| copper carbonate | 1 part by weight |
| copper arsenite | 1 part by weight |
| nonanoic acid | 2 parts by weight |
| aqueous ammonia solution (7%) | 96 parts by weight |

Preservative Treatment of Wood Products

The treating solution described above was used to treat lumber and log specimens by a pressure impregnation process. The specimens used and the treating schedule were similar to those described in Example V.

EXAMPLE VIII

Saturated solutions of the copper salts along with the organic acidic component, e.g. decanoic acid, were prepared in concentrated aqueous ammonia solution (28%) at room temperature. The required amount of these solutions was mixed with additional decanoic acid, water and concentrated ammonia solution (28%) to give the following formulation:

| | |
|---|---|
| copper carbonate | 1 part by weight |
| copper arsenate | 2 parts by weight |
| decanoic acid | 3 parts by weight |
| aqueous ammonia solution (7%) | 94 parts by weight |

Preservative Treatment of Wood Products

The treating solution described was used to treat white spruce round wood specimens.

| | |
|---|---|
| Dimensions | 7 inches diameter × 48 inches long |
| Moisture content | 40% |

The specimens were loaded into a pressure vessel and evacuated to 26½ in. Hg and maintained under vacuum for thirty minutes. The vacuum was lowered to 20 in. Hg with ammonia gas for 10 minutes and then returned to 26½ in. Hg for a further 20 minutes. This process of flushing was repeated three times to give a total period of evacuation of 2 hours. The vacuum in the treating vessel was reduced to 1 in. Hg and the treating solution was added. The pressure in the vessel was raised to 100 p.s.i. with air and was maintained at this pressure for 5 hours to give a treating schedule of 7 hours.

Over the first four hours of the process (two hours vacuum and two hours pressure), the temperature in the treating vessel was raised from 75°F. to 180°F. The temperature was reduced continuously over the last three hours of the process to 100°F.

The retention of treating solution and the depth of penetration in the wood specimens were determined 24 inches from the ends of the specimens.

| | |
|---|---|
| Retention | 15 lbs./cu.ft. |
| Penetration (in radial direction) | 1.2 inches |

EXAMPLE IX

Three hundred white spruce poles (18 ft. long) were pressure treated using a preservative composition according to an aspect of the present invention, whose components (in parts by weight) were:
  3.5 parts basic copper carbonate
  1.8 parts ammonium bicarbonate
  2.0 parts arsenic acid (71% arsenic pentoxide)
dissolved into 100 parts of aqueous ammonia solution containing 7% $NH_3$. This solution contains 5% of salts and can also be prepared in 50% concentrate, which can be diluted with water to the final concentration. The poles prior to treatment had an initial moisture content of from 20 to 45%. The poles were treated according to the following treating schedule:

Two hrs. steaming of the poles in a closed treating retort was followed by 1 hr. of vacuum (27 in.). Then, the retort was filled with preservative and a pressure of 150 p.s.i. was built up. The temperature of the treating solution was maintained between 120° and 135° F. by means of steam heated coils at the bottom of the treating retort. After 12 hrs. of pressure period, the pressure was released and the excess preservative was drained.

From the weight of the individual pole before and after treatment, the preservative uptake was defined and expressed as retention per volume of treated pole. The depth of preservative penetration was tested by borings taken at the top, middle and butt of the pole.

It was found that the minimum, mean and maximum preservative retention (calculated from 150 treated poles) was 11.7–13.6–18.9 pounds per cubic foot respectively.

It was also found that the minimum, mean and maximum depth of preservative penetration from borings was 0.6–0.88–1.25 inches respectively.

From other treatment tests on white spruce pole sections having a moisture content of 100–120%, it was found that kiln drying of material was not necessary. Air pre-seasoned poles can be treated to a sufficient depth of penetration and to a reliable level of retention.

COMPARATIVE EXAMPLE A

Figure 1:
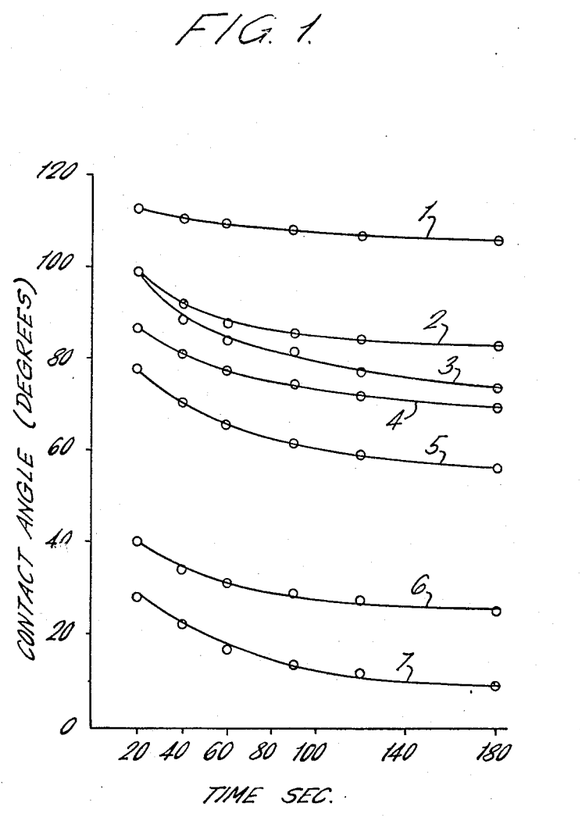
FIG. 1 is a graph showing the contact angles of water on red pine wood treated with various wood treating compositions, with contact angle (in degrees) as ordinate and time of wetting (in minutes) as abscissa, to give an indication of water repellency.

The water repellency of wood treated with various zinc-containing and copper-containing treating compositions was tested by measurement of the contact angle between the surface of treated wood and water. The data were plotted with contact angle as ordinate against time (in seconds) as abscissa during which the measurements were carried out. The results are shown graphically in FIG. 1. In the graph:

Curve No. 1 is a curve using copper carbonate (2%)
Curve No. 2 is a curve using copper arsenate (%) + copper carbonate (3%) (an embodiment of this invention)
Curve No. 3 is a curve using chromated copper arsenate (3%)
Curve No. 4 is a curve using copper chromate (3%)
Curve No. 5 is a curve using zinc orthoarsenate (3%)
Curve No. 6 is a curve using copper orthoarsenate (3%)
Curve No. 7 is a curve of non-treated pine wood control.

The higher the contact angle holding for a certain time period, the better the water repellency of the treated wood.

It is seen that the composition of an embodiment of this invention provides treated wood which is more water repellant than other compositions including the conventionally used CCA (Curve No. 3).

COMPARATIVE EXAMPLE B

Figure 2:
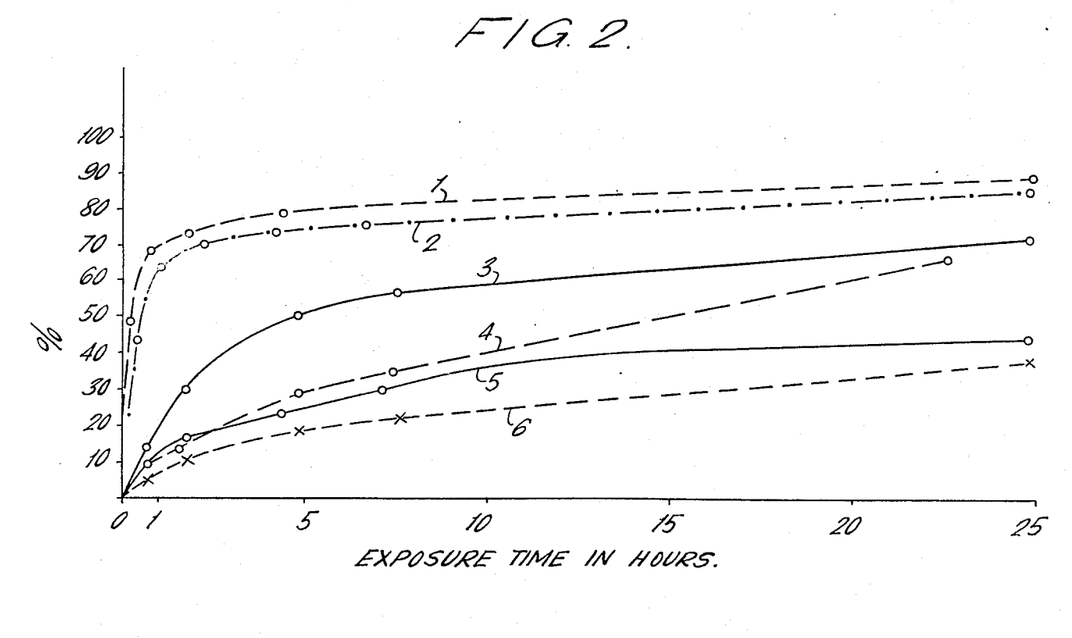
FIG. 2 is a graph showing resistance to water uptake, on nontreated red pine (a control) and on red pine substrates after exposure to various treating compositions, with water uptake (as percentage of oven dry weight) as ordinate, and exposure time (in hours) as abscissa, to give an indication of water repellency.

The water uptake by red pine treated with various compositions of this invention, as well as with CCA-C was also tested in order to show water repellency of wood treated with various preservatives. (CCA-C is the well-known designation for chromated copper arsenate). The results are shown in FIG. 2. In the graph, Curve No. 1 is the graph of an untreated red pine control.

Curve No. 2 is the graph using a composition of copper arsenate (1%) without any water repellant additive.

Curve No. 3 is the graph using copper chrome arsenate (3%).

Curve No.

The clearly superior results are shown in the Table below. the graph using zinc arsenate (3%) + zinc carbonate (3%) (an embodiment of this invention).

Curve No. 5 is the graph using zinc carbonate (3%).

Curve No. 6 is the graph using copper arsenate (3)% + decanoic acid (3%) (an embodiment of this invention).

As seen in FIG. 2, wood treated with the compositions of aspects of this invention has a lower water uptake after treatment than wood treated with the traditional CCA-C preservative (Curve No. 3).

COMPARATIVE EXAMPLE C

The penetration of various compositions of the present invention into non-treated white spruce (a difficult-to-penetrate refractory species) was compared against CCA-C and water. The penetration was carried out on oven dry samples of white spruce and expressed by per cent liquid uptake. The results are shown graphically in FIG. 3. In the graph, Curve No. 1 is the graph using zinc arsenate (1%) + zinc carbonate (3%) of an embodiment of this invention, Curve No. 2 is the graph using zinc arsenate (3%) + decanoic acid (1%) of an embodiment of this invention, Curve No. 3 is the graph using copper arsenate (3%) + decanoic acid (1%) of an embodiment of this invention, Curve No. 4 is the graph using copper arsenate (1%) + copper carbonate (2%) of an embodiment of this invention, Curve No. 5 is the graph using distilled water as a control, and Curve No. 6 is the graph using chopper chrome arsenate (3%).

Figure 3:
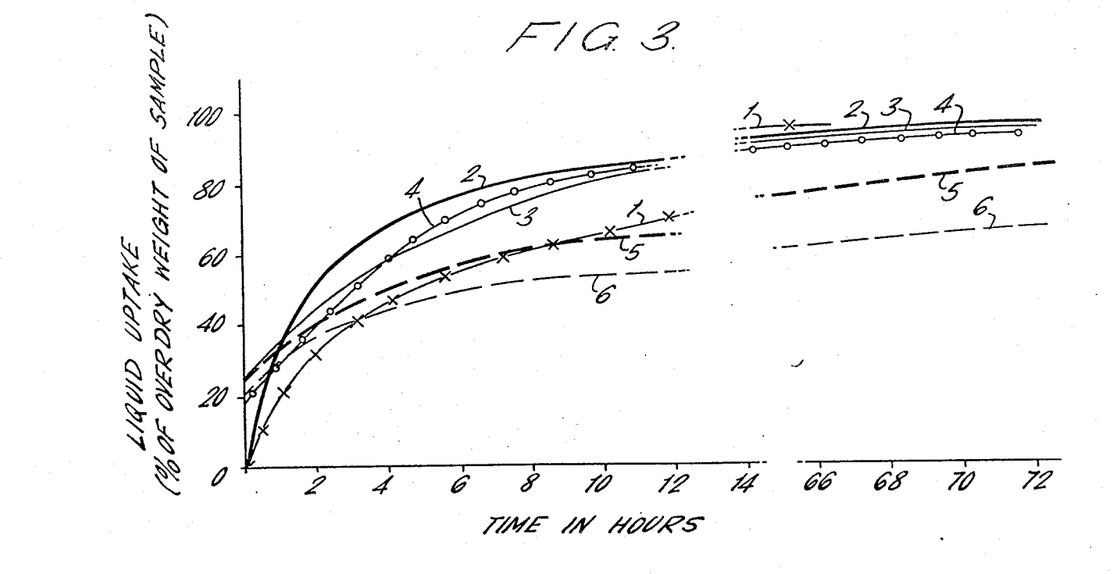
FIG. 3 is a graph showing penetration of preservative into white spruce (a refractory species) with liquid content (% of oven dry weight) as ordinate, and immersion time (hours) as abscissa, to give an indication of preservative penetration.

As seen from FIG. 3, as compared with CCA-C, commonly used in preservation practice at the present time, and when compared to distilled water, the compositions of aspects of this invention show faster and higher preservative penetration by wood samles, and approximately the same preservative penetration as for the best presently known preservatives.

COMPARATIVE EXAMPLE D

Resistance to Fungal Attack

The compositions of this invention, i.e. both the copper arsenate-ammonia complex system with water-repellent additives and the 1412-61 arsenate-ammonia complex system with water-repellent additives, were tested according to AWPA Standard M10, as follows: End-matched specimens were impregnated with preservative solutions of different concentrations. After drying the blocks were sterilized and pairs of blocks treated with the preservative were placed in jars containing 3-week old cultures of the test fungi. Two controls were used, one treated with distilled water, the other with distilled water containing ammonia. The jars were incubated for 12 weeks under standard conditions. Three pairs of blocks were used as a treatment group and the weight loss of wood was calculated from the oven dry weight of the wood before impregnation and after incubation. In the first experiments two test fungi were used: *Coniophora puteana* (A 328) and *Poria monticola* (A 189, Madison 698). This latter fungus is known for its tolerance to copper and zinc compounds and is recommended by ASTM D 1412-61 as a test fungus.

*Coniophora puteana* was selected on the basis of detoxication studies and toxicity tests carried out in this laboratory over the last several years. This fungus is a common cause of decay and is widespread throughout North America and Europe. It is used commonly throughout Europe and Australia as a test fungus as it grows well under a variety of conditions and shows a high level of resistance to a broad spectrum of fungicides.

Figure 4:
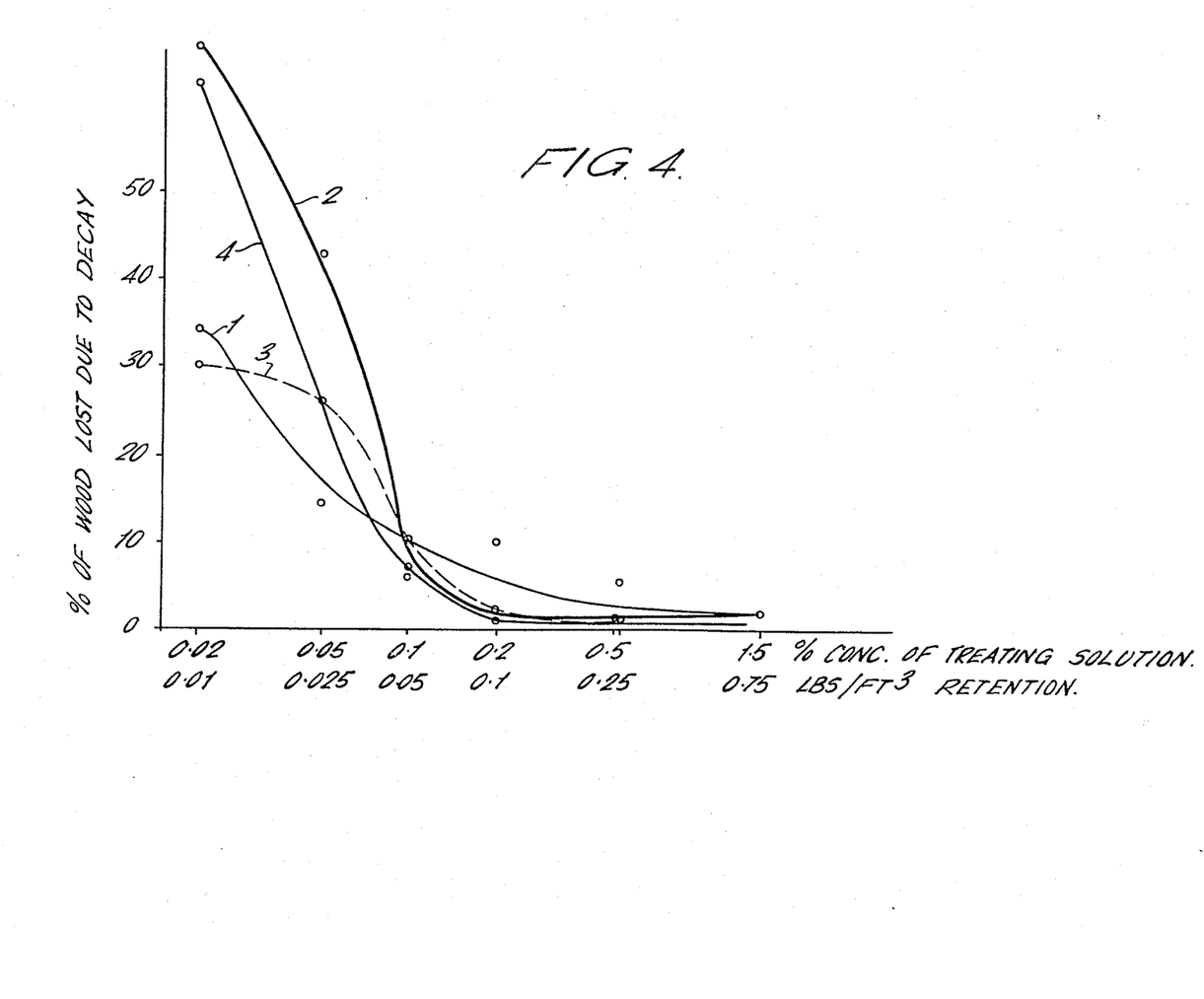
FIG. 4 is a graph showing the loss of wood due to decay (as ordinate) and percent concentration of treating solution (as abscissa) to give an indication of resistance to bacterial attack.

The results of the tests, where the fungus under test was *Coniophora puteana* or *Poria monticola* are shown in FIG. 4. In the graph, Curves Nos. 1 and 2 are graphs using a zinc preservative composition of one embodiment of this invention, with Curve No. 1 showing the effect on *Coniophora puteana*, and Curve No. 2 showing the effect on *Poria monticola*. Curves Nos. 3 and 4 are graphs using a copper preservative composition of one embodiment of this invention, with Curve No. 3 showing the effect on *Coniophora puteana*, and Curve No. 4 showing the effect on *Poria monticola*. It is seen that the percentage wood loss when the concentration of the treating solution was in excess of 0.1% by weight (corresponding to a retention in excess of 0.05 lbs/ft$^3$) was negligible for both fungal species. It is further to be noted that the copper system showed a higher level of toxicity and was equally toxic to both fungi and gave a threshold value of approximately 0.1 lb/ft$^3$. The zinc system was quite toxic to the *Poria monticola* with a threshold value of approximately 0.05 lb/ft$^3$ but was less toxic to *Coniophora puteana* having a threshold value of approximately 0.7 pounds per cubic foot. In this same series of tests, a comparative test using pentachlorophenol as a standard resulted in a threshold value of 0.26 lb/ft$^3$ for *Poria monticola* and 0.9 lb/ft$^3$ for *Coniophora puteana*.

COMPARATIVE EXAMPLE E

Glow Combustion Resistance

The glow combustion resistance was tested by the glow combustion test for sawdust treated with CCA-A, with one embodiment of a zinc arsenate-ammonia complex system of this invention, and with untreated sawdust. The test was carried out as follows: Spruce sawdust was impregnated with a 3% solution of each of the compositions being tested. From each of these samples, oven dried discs were prepared. The flame from a Bunsen burner was applied 2 inches beneath the disc for 30 seconds. After glowing in the disc ceased, the percentage weight loss was determined.

TABLE I

| Spruce - treated with: | Glow Combustion Test (Sawdust) Spruce | | |
|---|---|---|---|
| | % Weight Loss due to Glow Combustion | | |
| | Minimum | Average | Maximum |
| CCA-A (Copper chrome arsenate) | 93.9% | 96.34% | 99.7% |
| Zn preservative of an embodiment of this invention | 5.47% | 22.76% | 24.9% |
| Control (non-treated) | 14.5% | 21.29% | 23.1% |

It is seen that the percentage weight loss after treatment with CCA-A amounts to an average of about 96% while the percentage weight loss after treatment with a zinc composition according to the present invention is an average of about 23%, about equal to the control, untreated samples.

COMPARATIVE EXAMPLE F

U.S. Pat. No. 2,423,619

Copper and zinc soap solutions in ammonia were prepared as directed in U.S. Pat. No. 2,423,619 and wood samples were brushed with the solutions. The samples were then top-coated with a conventional exterior acrylic latex. A cross-hatch test indicated that samples brushed with zinc soap solutions adversely affected the adhesion of the latex to the substrate. The copper soap solution treated sample showed poor adhesion, but was appreciably better than the zinc soap-treated sample.

In another experiment, brushed and top-coated cedar wood samples were subjected to high humidity gradients. Within two to three hours, the copper soap-treated samples were stained due to extractive bleed-through while the zinc soap-treated samples blistered badly.

As a comparison, similar wood samples treated with the composition of this invention did not exhibit any bleed-through of extractives or blistering over a period of 6 to 8 hours under identical conditions. In addition, the adhesion of the latex top coat to the samples treated with the composition of this invention was good.

COMPARATIVE EXAMPLE G

U.S. Pat. No. 2,530,458

The patent provides a coating composition containing tertiary zinc orthophosphate or tertiary zinc ortho-arsenate, in amounts of 25-125 parts and 30-35% hydrous ammonia, in amounts of 100 parts.

¾inch cubes of red pine were impregnated with 3% solutions of zinc orthophosphate and zinc orthoarsenate in which the ratio of salt and ammonia was within the ratios described in the above-noted patent. These blocks were compared with ¾inch red pine blocks heated with a 3% solution of the composition described in Example II, for water pickup. Both the rate of water pickup and the amount of water picked up over a period of 10 hours were very much lower in the case of the blocks treated with the composition of Example II. The order of difference was similar to that seen in FIG. 2.

COMPARATIVE EXAMPLE H

U.S. Pat. No. 2,768,910

This patent provides ammoniacal solutions of polycarboxylic acids, e.g. a 20% ammoniacal solution of phthalic acid.

Red pine locks impregnated with a 3% ammoniacal solution of phthalic acid were compared with red pine blocks treated with a 3% solution of the composition shown in Example II. The blocks were tested using the procedure described in Comparative Example E. The toxicity to the wood destroying fungi of the phthalic acid treated blocks was negligble compared to the blocks treated with the composition of Example II.

COMPARATIVE EXAMPLE I

U.S. Pat. No. 2,772,263

This patent provides a treating solution comprising a metal (e.g. zinc or copper) rosin ammonium phenoxide complex-metal carboxylic acid soap compound.

A copper soap of the rosin phenoxide carboxylic acid compound described in the above-identified United States patent was prepared. The soap separated from solution and was insoluble. The supernatant liquid was compared against 3% solutions of the compositions described in Examples II and V by the procedure described in Comparative Example D. The toxicity to Wood destroying fungi of the supernatant was negligible compared to the solutions of Examples II and V.

COMPARATIVE EXAMPLE J

U.S. Pat. No. 2,414,661

This patent describes a treating solution which includes the product resulting from the reaction of copper or zinc sulfate or carbonate with an alkali (e.g. ammonium hydroxide) and a soya bean protein or a soap of a fatty acid, in order to precipitate a basic copper zinc sulfate proteinate.

A copper soap as described in the above-identified United States patent was prepared. The soap separated from solution and was insoluble. The supernatant liquid was compared against 3% solutions of the compositions described in Examples II and V by the procedure described in Comparative Example D. The toxicity to wood destroying fungi of the supernatant was negligible compared to the solutions of Examples II and V.

We claim:
1. A wood treating composition comprising an aqueous solution containing:
    a. a normally water-insoluble compound selected from the group consisting of zinc arsenate, zinc arsenite, copper arsenate, and copper arsenite and mixtures thereof in an amount of about 0.1 to about 4% by weight (as Zn or Cu metal) of the total aqueous solution;
    b. about 0.15 to about 10% by weight of the total aqueous solution of a water-repellent component comprising one of
        i. a water-insoluble organic acidic compound having a solubility ≥ about 0.2% and in concentrated aqueous ammonia, said water-insoluble organic acidic compound being selected from the group consisting of acid esters of phosphoric acid with monohydric alcohols and having an acid value between about 200 and about 500, and mixtures thereof, in an amount of about 0 to about 200% of the zinc or copper, or ii. a combination of said selected organic acidic compound and a carbonate or bicarbonate ion selected from the group consisting of zinc carbonate, zinc bicarbonate, copper carbonate and copper bicarbonate in an amount of about 0 to about 150% of the zinc or copper; and c. ammonia, in an amount of about 1 to about 28% by weight of the total aqueous solution; the ammonia being sufficient to solubilize said normally water-insoluble salt of zinc or copper and said normally water-insoluble water-repellent compound.

2. The wood treating composition of claim 1, wherein the organic acidic compound is selected from: acid esters of phosphoric acid with saturated monohydric alcohols having between about 8 and about 15 carbon atoms; and acid esters of phosphoric acid with unsaturated monohydric alcohols having between 8 and about 15 carbon atoms.

3. The wood treating composition of claim 1, having a pH of about 9 or more, and comprising an aqueous solution containing:
A. at least one of
  a. copper ammonium arsenate,
  b. copper ammonium arsenite,
  c. zinc ammonium arsenate, or
  d. zinc ammonium arsenite; and
B. anions of said selected organic acidic component.

4. The wood treating composition of claim 1, having a pH of about 9 of more, and comprising an aqueous solution containing:
A. at least one of
  a. copper ammonium arsenate,
  b. copper ammonium arsenite,
  c. zinc ammonium arsenate, or
  d. zinc ammonium arsenite; and
B. anions of both
  e. said selected organic acidic component, and
  f. said carbonate or bicarbonate.

5. The wood treating composition of claim 4, wherein the composition contains acid esters of phosphoric acids with monohydric alcohols, and zinc carbonate or copper carbonate.

6. The wood treating composition of claim 5, wherein the composition contains copper arsenate and zinc arsenate.

7. The wood treating composition of claim 5, wherein the composition contains zinc arsenite and copper arsenite.

8. The wood treating composition of claim 4, selected from the group consisting of:
a. zinc arsenate
  zinc carbonate
  monododecyl phosphate
  aqueous ammonia solution (7% by weight)
b. zinc arsenate
  zinc oxide
  ammonium carbonate
  dibutyl phosphate
  aqueous ammonia solution (10% by weight) and
c. copper carbonate
  copper arsenite
  dihexyl phosphate
  aqueous ammonia solution (7% by weight)

9. A concentrated aqueous solution comprising a saturated solution, in concentrated aqueous ammonia of about 28% concentration, of
I.
  a. copper arsenate or
  b. copper arsenite, the copper being present in the amount of about 15 to about 25%;
  c. zinc arsenate or
  d. zinc arsenite, the zinc being present in the amount of about 25 to about 80%;
  e. a mixture of copper arsenate and zinc arsenate or copper arsenite and zinc arsenite, the zinc and copper in the mixture being present in the amount of about 25 to about 5%; and
II. an organic acid component having a solubility ≥ about 0.2% and in concentrated aqueous ammonia, said water-insoluble organic acidic compound being selected from the group consisting of acid esters of phosphoric acid with monohydric alcohols and having an acid value between about 200 and about 500, and mixtures thereof.

10. A concentrated aqueous solution comprising a saturated solution, in concentrated aqueous ammonia of about 28% concentration, of
I.
  a. copper arsenate or
  b. copper arsenite, the copper being present in the amount of about 15 to about 25%;
  c. zinc arsenate or
  d. zinc arsenite, the zinc being present in the amount of about 25 to about 80%;
  e. a mixture of copper arsenate and zinc arsenate or copper arsenite and zinc arsenite, the zinc and copper in the mixture being present in the amount of about 25 to about 5%;
II. an organic acidic component having a solubility ≥ about 0.2% and in concentrated aqueous ammonia, said water-insoluble organic acidic compound being selected from the group consisting of acid esters of phosphoric acid with monohydric alcohols and having an acid value between about 200 and about 500, and mixtures thereof, and
III. one or more of
  e. copper carbonate
  f. copper bicarbonate
  g. zinc carbonate or
  h. zinc bicarbonate.

* * * * *

UNITED STATES PATENT OFFICE
CERTIFICATE OF CORRECTION

Patent No. 3,945,835             Dated  Mar. 23, 1976

Inventor(s)  Michael R. Clarke et al.

It is certified that error appears in the above-identified patent and that said Letters Patent are hereby corrected as shown below:

Column 4, line 66:  rewrite "comprsing" as --- comprising ---.

Column 7, line 25:  rewrite "solution" as --- solutions ---.

Column 7, line 26:  before "about", insert --- $\geq$ ---.

Column 11, line 11: rewrite "presure" as --- pressure ---.

Column 15, line 63: rewrite "samles" as --- samples ---.

Column 16, line 6:  after "drying", insert a comma (-- , --).

Column 20, lines 22 and 43:  replace "5%" with --- 50% ---.

Signed and Sealed this

Twenty-third Day of November 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,945,835          Dated March 23, 1976

Inventor(s) Michael R. Clarke et al.

It is certified that error appears in the above-identified patent and that said Letters Patent are hereby corrected as shown below:

Abstract, lines 7 and 8: delete in entirety and replace with

-- phoric acid or both such acid ester of phosphoric acid and a carbonate or bicarbonate, which anions have --.

Signed and Sealed this

Fifteenth Day of February 1977

[SEAL]

Attest:

RUTH C. MASON
Attesting Officer

C. MARSHALL DANN
Commissioner of Patents and Trademarks